United States Patent [19]

Callahan

[11] 4,037,481
[45] July 26, 1977

[54] DEVICE FOR MEASURING THE DENSITY OF LIQUIDS

[75] Inventor: George Edgar Callahan, Dusseldorf-Nord, Germany

[73] Assignee: Helmut Naumann, Dusseldorf, Germany

[21] Appl. No.: 576,646

[22] Filed: May 12, 1975

[30] Foreign Application Priority Data

May 21, 1974 Switzerland ............... 6972/74

[51] Int. Cl.² ................................................ G01N 9/16
[52] U.S. Cl. ........................................................ 73/454
[58] Field of Search ............... 73/451, 441, 454, 32 R

[56] References Cited

U.S. PATENT DOCUMENTS

| 2,129,617 | 9/1938 | Hill | 73/451 |
|---|---|---|---|
| 2,168,353 | 8/1939 | Linebarger | 73/451 |
| 2,212,809 | 8/1940 | Ericson | 73/451 |

FOREIGN PATENT DOCUMENTS

| 474,014 | 10/1937 | United Kingdom | 73/454 |
|---|---|---|---|
| 410,935 | 5/1934 | United Kingdom | 73/451 |

Primary Examiner—Richard C. Queisser
Assistant Examiner—Stephen A. Kreitman
Attorney, Agent, or Firm—Larson, Taylor and Hinds

[57] ABSTRACT

Portable devices for measuring the density of liquids are described. In each of these, a floating element and a reference element are pivotally mounted on a horizontal axis, the floating element being in a casing containing the liquid and having a transparency through which the floating element can be viewed. The reference element may be either outside or inside the casing and is arranged so that the gravitational force, or combined gravitational and buoyant forces thereon, maintain it in stable equilibrium about the axis, and so in a fixed position in a vertical plane irrespectively of the position of the casing in that plane. In one example the floating element is marked with a scale and the reference element is an indicator arm also immersed in the liquid and balanced by an extension on the opposite side of the axis. In another example the floating element is an indicator arm and the reference element a pendulum member marked with a scale.

8 Claims, 8 Drawing Figures

DEVICE FOR MEASURING THE DENSITY OF LIQUIDS

FIELD OF THE INVENTION

The present invention relates to a device for measuring the density of liquids, comprising a chamber to be filled with the liquid in which there is provided a floating element which can be swivelled up and down about an axis wherein the inclination angle of the floating element obtained by buoyancy in the liquid can be read in relation to a reference element.

DESCRIPTION OF THE PRIOR ART

In a heavy liquid, the buoyancy is high, and a steeper inclination angle is obtained than in a lighter liquid. The inclination angle accordingly serves as measure for the dnsity of the liquid. Density measuring devices are known which comprise a floating indicator the inclination angle of which can be read on a scale rigidly fixed on the casing of the instrument. The inclination angle of the floating indicator depends on the density of the liquid surrounding the indicator and on the direction of terrestrial gravity. With liquids of equal density, the floating indicator always forms the same angle with respect to a vertical line. Accordingly, this inclination angle does not depend on movements effected by the casing of the instrument contained the luquid. On the other hand, the scale is moved simultaneously with the casing of the instrument. In order to have a fixed reference position and to avoid wrong readings, it is necessary to position the scale or alternatively the instrument exactly with respect to the vertical. This is particularly indispensable with hand-carried density measuring instruments. For this purpose, known density measuring instruments are quipped with additional means for indicating their position, for example a water-level or a pendulum indicator, as shown in an embodiment of U.S. Pat. No. Des. 220,125. While measuring the density, such an instrument is first oriented with respect to the vertical and then the position of the floating indicator read on the scale. The necessity to effect readings on the scale while keeping at the same time the device in a vertical position and observing the pendulum indicator causes uncertainties in the use of such density measuring devices and in practice frequently leads to mistakes.

SUMMARY OF THE INVENTION

It is the purpose of the present invention to provide a density measuring device of the type described above in whih the correct reading of the inclination angle of the floating element does not depend on a particular position of the device.

According to the present invention, this problem is resolved by a reference element which can be swivelled around the same axis and which is shaped so that it remains, in the measuring position of the density measuring device, in one and the same equilibrium angle with respect to the vertical.

Accordingly, the reference element always is in an invariable position with respect to the vertical, which cannot be influenced by the movements of the device while the position of the floating element is varied with respect to the vertical by the density of the liquid, but does not either depend on movements of the measuring device. The relative position of the two elements accordingly only depends on the density of the liquid. Accordingly, it is not necessary to position the device exactly with respect to the vertical and particularly unnecessary to make two observations, namely to read the position of the two elements and at the same time to survey the orientation of the measuring device.

Reading of the determined density values or the values derived therefrom is effected on a scale. Two embodiments of the invention are possible. In one of the embodiments the scale is fixed on the reference element and the floating element provided in the form of and indicator arm or provided with scale markings. In the other embodiment, the reverse is the case.

In a first embodiment, the reference element may be provided outside the chamber.

Its center of gravity is then preferably below the axis. In this case, it forms a pendulum hanging downwards from the axis and always takes a position in which the center of gravity lies exactly vertically under the axis. By appropriate shaping of the casing of the density measuring device, care can be taken that the reference element, while handling the device, is not impeded in its free movement.

It is however also possible to arrange the reference element in the chamber so that it is accordingly in the liquid during the measuring operation.

The center of all the forces acting on the reference element which then results from the gravity center and from the buoyancy center may then by situated at a certain distance below the axis.

The complete reference element is then heavier than the displaced liquid volume and therefore hangs below the pivotal axis.

The center of the forces acting on the reference element which results from the center of gravity and from the center of buoyancy may however alternatively lie above the axis, the reference element being situated in the chamber.

The reference element is then lighter than the displaced liquid; it floats above the pivotal axis and is only prevented from moving upwards while the liquid is being drawn into the device by the fixing of the pivotal axis.

In both embodiments, the existence of a space between the force center and the axis means that the reference element is in a stable equilibrium. This should be true for the whole density range of the liquids the density of which is to be measured.

Such a reference element may for example be realised by using a reference element which protrudes away from the axis on both sides and so that the turning moments exerted on the reference element by the buoyancy are of the same amount, but in opposite direction.

In order to obtain space economies and for obtaining a smaller chamber volume, it is advantageous if the reference element and the floating element are of flat shape and are arranged in close proximity to each other in parallel planes on the axis.

It is possible thereby to use a flat chamber whereby the liquid quantity necessary for filling and measuring is reduced. Also, parallax is reduced.

The liquid the density of which is to be determined, according to the present invention, may be filled into the chamber by means of vacuum in a known manner by means of a compressible hollow element connected with the chamber. The connection channel between the hollow element and the chamber enters into the chamber at the top thereof and into the hollow element at the bottom thereof so that the chamber can be filled completely by suction and so that liquid which may have penetrated into the hollow element can be forced out therefrom.

In order to obtain a compact instrument the surface of which is as smooth as possible, it is advantageous if the compressible hollow element is fixed immediatly on the casing and if its exterior shape merges into the outline thereof.

It is furthermore desirable for the hollow element to constitute a handle of the density measuring device since the hollow element must anyhow be held by hand. To enable it to be gripped securely, the hollow element may comprise, on its outer face, projections or ribs.

In particular embodiment, the hollow element is arranged on the side of the chamber lying opposite the scale division and the indicator with respect to the pivotal axis.

This facilitates handling insofar as the scale division is just in front of the eyes when the hollow element is held by the user.

In order to obtain precise measurements, it is advantageous if the hollow element and the chamber are connected by a channel which ends in the lowest part the hollow element and in the highest part of the chamber when the device is in its measuring position because, in this manner, inaccuracies of the measuring result due to residual liquid in the hollow element can be avoided. It is important for obtaining exact measuring results that the chamber should be completely filled during the measuring operation and that air bubbles do not adhere either to the floating element for to the reference element. It is advantageous if, for this purpose, a closable tap is provided which can be connected at one end with a short tube and at the other end with a channel ending in the chamber. If, after aspiration of the liquid, the density of which is to be measured, the tap is closed, the subsequent aspiration of air, or the formation of air bubbles, and emptying of the chamber can be avoided.

For storage, the density measuring device may be hung on a wall and, for this purpose, is provided with a hanger.

DESCRIPTION OF THE DRAWINGS

In order that the invention may be clearly understood and readily carried into effect density measuring device in accordance therewith will now be described by way of example, with reference to the accompanying drawings, in which.

Figure 1:
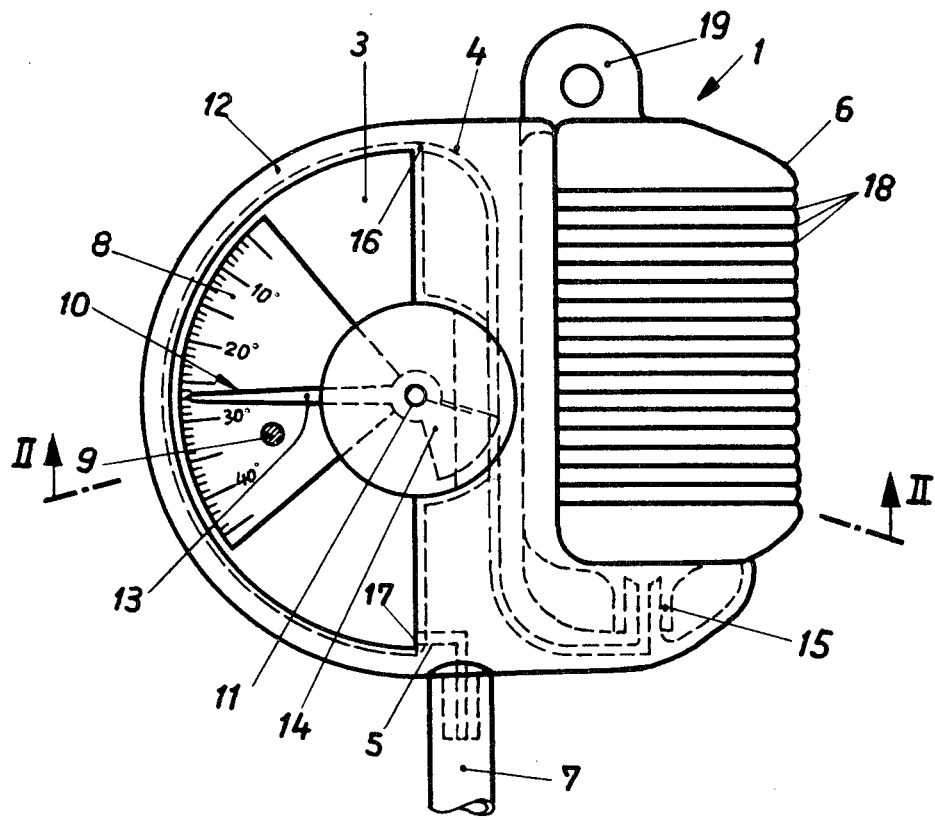
FIG. 1 is a front elevation of a density measuring device for liquids.
Figure 2:
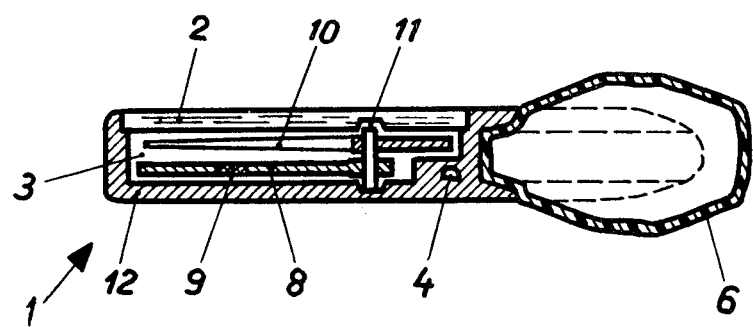
FIG. 2 is a section along line II — II in FIG. 1.

The density measuring device, designated as a whole as 1 in FIGS. 1 - 4 comprises a casing 12 of synthetic plastic material or of another suitable material which cannot be destroyed by the liquid in the density of which is to be determined. In the casing 12, there is provided a chamber 3 which can be filled with liquid and which contains a scale segment 8, forming a floating element, as well as an indicator arm 10 forming the reference element. The chamber 3 is covered by a transparent plate 2 so that the scale segment 8 and the indicator arm 10 are visible in the chamber. Also the material of casing 12 may be transparent.

The scale segment 8 and the indicator arm 10 are pivotally supported beside each other on a spindle 11 provided in casing 12. The scale segment 8 forms a circular sector supported at the center at which its arcuate edge is struck, and which has a compensating weight 9 for maintaining its equilibruim. The indicator arm 10 consists of the proper arm 13 movable over the scale segment 8 and of a part 14 protruding to the other side with respect to spindle 11. The relative positions of the parts 13, 14 is such that the center of gravity of the indicator arm 10 lies below axis 11 so that the indicator arm 10 is in stable equilibrium. The center of action of the force which is the resultant of the buoyancy and force of gravity on the arm 10 is below spindle 11 for the liquids intended to be used, i.e. for example cooling water for internal combustion engines, containing varying quantities of anti-freezing agents. Parts 13 and 14 of the indicator arm 10 are compensated with respect to weight as well as with respect to buoyancy so that they produce equal turning moments around spindle 11 irrespectively of the density of the liquid being measured in chamber 3 and the indicator arm 10 is always maintained at the same angle with respect to the vertical. Alternatively the said center of action of the resultant force acting on the indicator arm 10 may be above the spindle 11 to maintain the arm in stable equilibrium.

The scale segment 8 does not have this compensation so that it assumes, in the chamber 3, different angles about the axis of spindle 11 with respect to the vertical and thus makes possible the determination of the densities of the liquids that are tested.

Filling of chamber 3 with the liquid the density of which is to be determined is effected by means of a resiliant compressible hollow element 6 which consists either of rubber or of synthetic elastic material. The hollow element 6 is connected to a channel 4 in casing 12 by means of a nozzle 15, the channel being connected with chamber 3 via orifice 16. The orifice 16 is arranged so that, when the density measuring device 1 is held upright and the axis 11 is horizontal, i.e. in the measuring position, it enters in the chamber 3 in its uppermost point.

At the lowermost point of chamber 3, when in the measuring position, a channel 5 enters chamber 3 at 17 and is connected by its other end with a short tube 7 by means of a closing tap 21, such as tap 21 described below with reference to FIG. 8.

For filling the chamber 3, the hollow element 6 is compressed by hand while the end of tube 7 is in the liquid to be tested. When releasing the hollow element 6, the element extends and produces subatmospheric pressure in chamber 3 by which liquid is aspirated into chamber 3 through tube 7, closing tap 21 and channel 5. The volume of the hollow element 6 is so chosen with respect to that of chamber 3 that one actuation of hollow element 6 is sufficient to fill chamber 3 with liquid.

After the chamber 3 has been filled, the closing tap 21 is closed by rotation of a projection 24 whereby neither air is sucked in nor liquid released.

When the chamber is filled with liquid, the density of the liquid can be read on the floating scale segment on any desired scale that has been marked thereon. In the example the scale is in Celsius degrees since this example relates to a density meter for testing cooling liquids for internal combustion engines. Celsius degrees indicate the lowest temperature at which the liquid will not freeze. Safety against freezing depends on the ratio between water and anti-freeze agent which ratio also determines the density of the liquid.

During the measuring operation, the density meter 1 can be held by the hollow element which, for this purpose, is provided with ribs 18. When holding the hollow element with the right hand, the scale segment 8 and the indicator arm 10 are easily seen just in front of the eyes.

Figure 3:
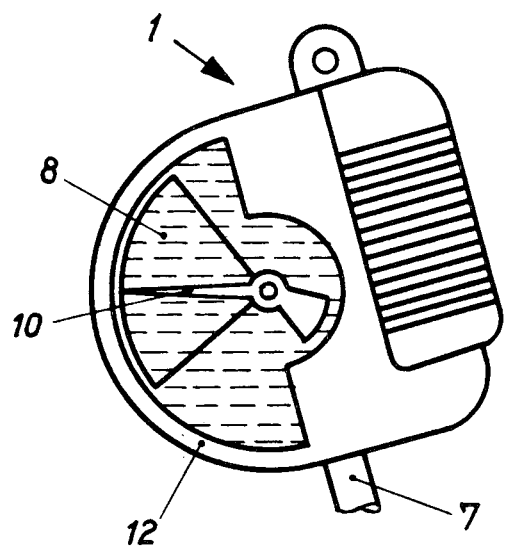
FIG. 3 and 4 are front elevations similar to FIG. 1 showing the measuring device located in different positions in a vertical plane.
Figure 4:
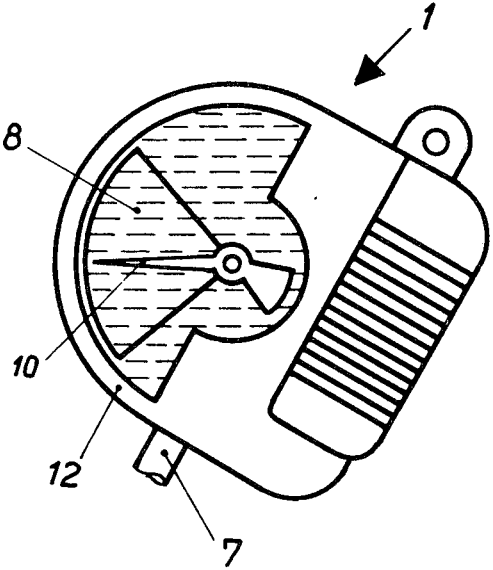

FIGS. 3 and 4 demonstrate the insensitivity of the arrangement to inclination of casing 12 in the vertical plane. Although, according to FIG. 3, the casing 12 is inclined to the left and, according to FIG. 4, to the right, the scale segment 8 and the pendulum arm 10 keep their unvaried respective positions in the liquid and with respect to the vertical.

On the upper part of casing 12, there is provided a hanger in the shape of a hand-up eye 19 by means of which the density measuring device can be hung up on a wall when not in use.

Figure 5:
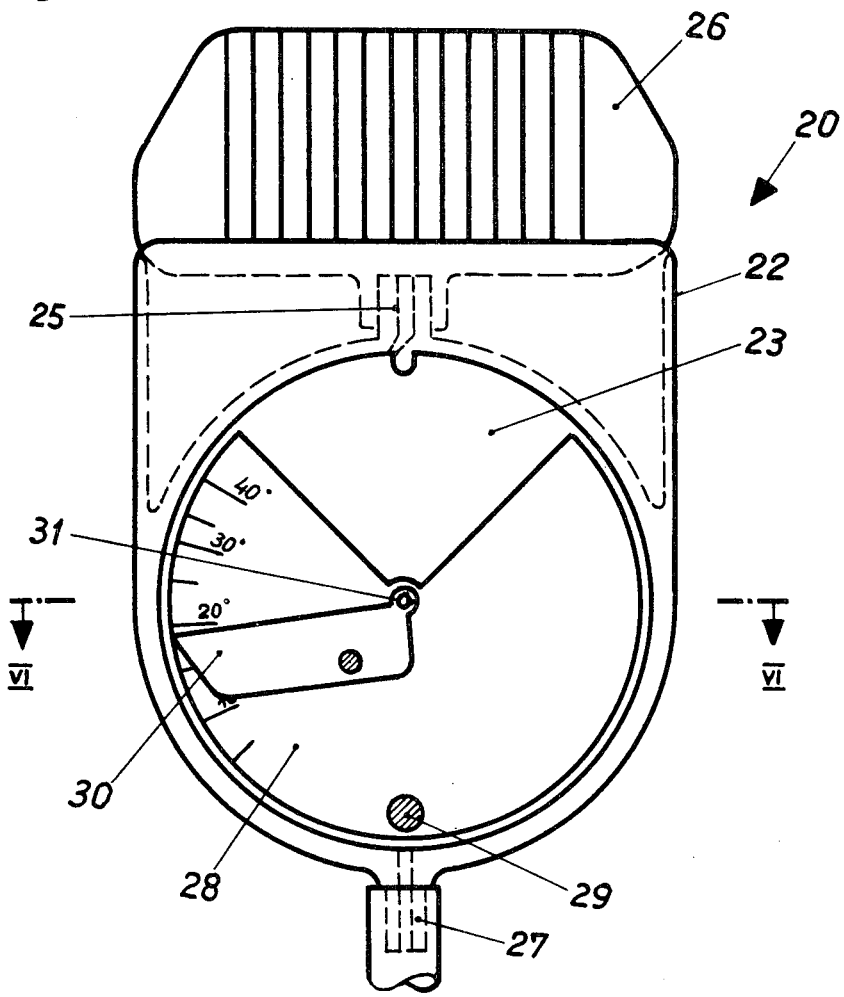
FIG. 5 is a front elevation of another density measuring device.
Figure 6:
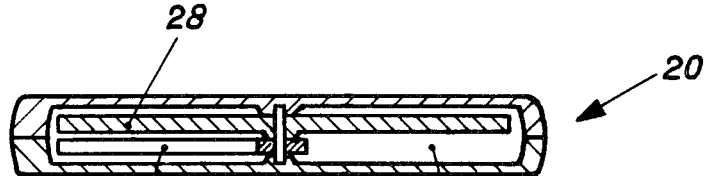
FIG. 6 is a section along line VI — VI in FIG. 5.

FIGS. 5 and 6 show a further density measuring device, designated as a whole by reference numeral 20, in which a floating indicator 30, provided in chamber 23 and pivoted about spindle 31, is provided on one side of spindle 31 and assumes various positions under the buoyancy effect of liquids of various densities. On the other hand, a scale segment 28 forming the reference element is loaded with weight 29 and is in stable equilibrium about the axis of spindle 31. Scale segment 28 and floating indicator 30 are flat plates which make it possible to use a flat chamber 23 as shown in FIG. 6.

Chamber 23 is filled by a hollow element 26 which is arranged above chamber 23 when in the measuring position. The hollow element 26 is placed immediately above the casing of density measuring device 20, and the contours of hollow element 26 and of casing 22 merge into each other. Connection channel 25 ends in the hollow element 26 at the lowermost part thereof, and extends into chamber 23 at the uppermost part thereof so that the chamber 23, during aspiration through aspirating tube 27, can be filled completely, but liquid which may have penetrated into hollow element 26 may also be forced downwards into the chamber 23 and out through aspiration tube 27.

Figure 7:
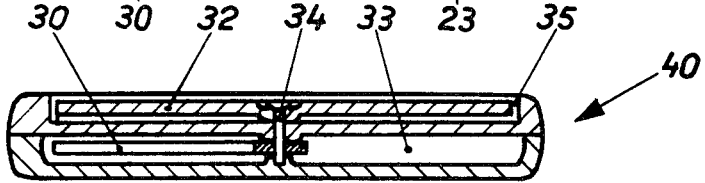
FIG. 7 is a section similar to that of FIG. 6 showing a modification of the device of FIG. 5.

FIG. 7 shows a modified density measuring device 40 which is different from density measuring device 20 in that the scale segment 32 is not arranged in chamber 33 together with floating indicator 30, but outside the chamber in a corresponding recess 35 in the casing of the density measuring device 40. The reference element 32 is pivoted about the same axis 34 as the floating indicator 30 and hangs freely in stable equilibrium on the axis 34.

Figure 8:
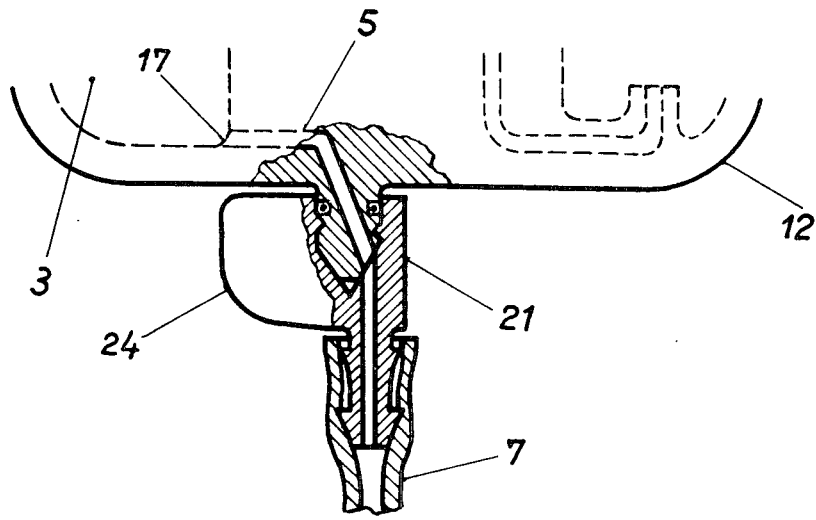
FIG. 8 is an elevation, partly in section showing a modification of the device of FIG. 1.

FIG. 8 shows a partial section through a modified embodiment of density measuring device 1 of FIG. 1. As shown, the density measuring device has on its casing 12 a closing tap 21 between channel 5 and tube 7. After chamber 3 has been filled, the stopping tap 21 is closed by rotation of projection 24 so that neither liquid may get out of nor air into the chamber.

I claim:

1. A portable device for measuring the density of liquids, comprising a casing having a chamber formed therein, a floating element pivotally mounted in said chamber to turn about an axis which is arranged to be horizontal when said device is being used to measure the density of a liquid, said floating element being formed as a scale member, a reference element pivotally mounted about said axis and exterior to said chamber, said reference element adapted to remain stable in equilibrium about said axis during said use, said reference element being formed as an indicator arm which comprises a proper arm extending on one side of said axis and being movable over the scale member and a balancing portion extending to the opposite side of said axis, the relative position of said proper arm and said balancing portion is such that the center of gravity of the indicator arm lies vertically below said axis thereby maintaining said indicator arm in stable equilibrium about said axis during said use, a resilient compressible hollow element for filling said chamber with a liquid of which the density is measured, said hollow element being formed with a channel means connecting the interior of said hollow element at the outlet of said channel means to said chamber at the inlet of said channel means, and said casing being formed with a further channel through which said chamber can be filled with said liquid, said hollow element being of such size that said chamber can be filled through said further channel by compression and release of said hollow element.

2. A device according to claim 1, wherein said hollow element constitutes a handle whereby the device may be held when measuring the density of a liquid 3. A device according to claim 1, comprising a short tube at the bottom of said chamber and with which said further channel communicates, and a tap mounted on said short tube for opening and closing the passage through said short tube, said outlet of said channel means being located at the top of said chamber.

4. A portable device for measuring the density of liquids, comprising a casing having a chamber formed therein, a floating element pivotally mounted in said chamber to turn about an axis which is arranged to be horizontal when said device is being used to measure the density of a liquid, said floating element being formed as a scale member, a reference element pivotally mounted about said axis and in said chamber, said reference element adapted to remain stable in equilibrium about said axis during said use, said reference element being formed as an indicator arm which comprises a proper arm extending on one side of said axis and being movable over the scale member and a balancing portion extending to the opposite side of said axis, the relative volumes and positions of said proper arm and said balancing portion are such that the center of gravity and the center of buoyancy of the indicator arm lie vertically outside said axis, thereby maintaining said indicator arm in stable equilibrium about said axis during said use, a resilient compressible hollow element for filling said chamber with a liquid of which the density is measured, said hollow element being formed with a channel means connecting the interior of said hollow element at the outlet of said channel means to said chamber at the inlet of said channel means, and said casing being formed with a further channel through which said chamber can be filled with said liquid, said hollow element being of such size that said chamber can be filled through said further channel by compression and release of said hollow element.

5. A device according to claim 4, wherein said hollow element constitutes a handle whereby the device may be held when measuring the density of a liquid.

6. A device according to claim 1, comprising a short tube at the bottom of said chamber and with which said further channel communicates, and a tap mounted on said short tube for opening and closing the passage through said short tube, said outlet of said channel means being located at the top of said chamber.

7. A device according to claim 4 wherein said scale member forms a circular sector supported in the center at which its arcuate edge is struck and which has a compensating weight for maintaining its equilibrium.

8. A device according to claim 1 wherein said scale member forms a circular sector supported in the center at which its arcuate edge is struck and which has a compensating weight for maintaining its equilibrium.

* * * * *